United States Patent [19]

Moore, Jr. et al.

[11] 4,248,219
[45] Feb. 3, 1981

[54] SCAVENGER SYSTEM FOR ANESTHESIA CIRCUITS

[75] Inventors: Robert W. Moore, Jr., Crosby, Tex.; Stanley C. Weinrich, 618 Diamondhead Blvd., Crosby, Tex. 77532

[73] Assignee: Stanley C. Weinrich, Crosby, Tex.

[21] Appl. No.: 50,328

[22] Filed: Jun. 20, 1979

[51] Int. Cl.³ .............................................. A61M 17/00
[52] U.S. Cl. ............................... 128/205.17; 128/910; 128/276
[58] Field of Search .............. 128/910, 205.13, 205.17, 128/204.18, 205.19, 276

[56] References Cited

U.S. PATENT DOCUMENTS

| 4,004,585 | 1/1977 | Boehringer | 128/205.17 |
| 4,112,940 | 9/1978 | Parkes | 128/910 |

Primary Examiner—Henry J. Recla
Attorney, Agent, or Firm—Ranseler O. Wyatt

[57] ABSTRACT

A scavenger system for anesthesia circuits having a breathing bag and an escape passageway in said bag, a pair of telescoping tubular components having slots therein and being rotatable to vary the opening created by the alignment of said slots, and a laterally extending parabolic conduit terminating in an enlarged areating chamber in which a vacuum is maintained to draw the gas out of said chamber without placing a negative pressure on the escape passageway.

5 Claims, 7 Drawing Figures

SCAVENGER SYSTEM FOR ANESTHESIA CIRCUITS

BACKGROUND OF THE INVENTION

In the previous application above referred to, the gas being used for an anesthetic is exhausted into the ambient atmosphere in the operating room and is capable of affecting the surgical personnel. It is an object of this invention to provide an exhaust valve for the anesthetic circuit that may be adjustable by the anesthetist as the operation proceeds, and that will assure removal of the gas from the operating area.

SUMMARY OF THE INVENTION

A scavenger system for an anesthesia circuit having a male and female compenent and a passageway therethrough, said components being rotatable relative to each other to open and close said passageway, and a laterally extending parabolic passageway having a tubular connection on said passageway terminating in an enlarged, aerated chamber on a vacuum is maintained to draw the gas out of the chamber without placing anegative pressure on the escape passageway.

DESCRIPTION OF THE PREFERRED EMBODIMENT

Figure 1:
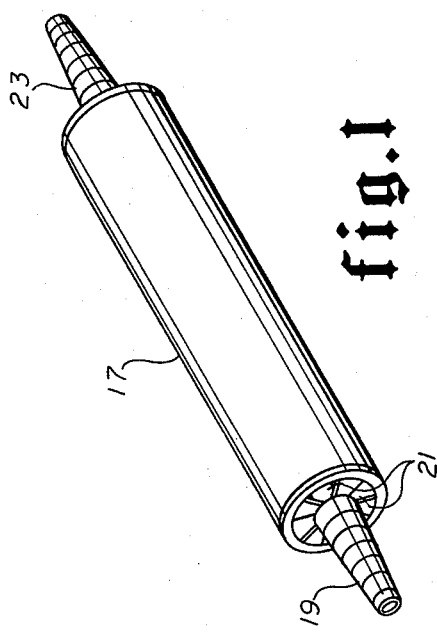
FIG. 1 is an elevational, perspective view of the enlarged chamber.
Figure 3:
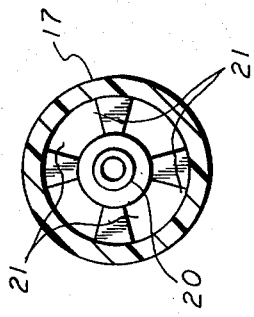
FIG. 3 is a cross sectional end view of the enlarged chamber, taken on the line 3—3 of FIG. 2.
Figure 2:
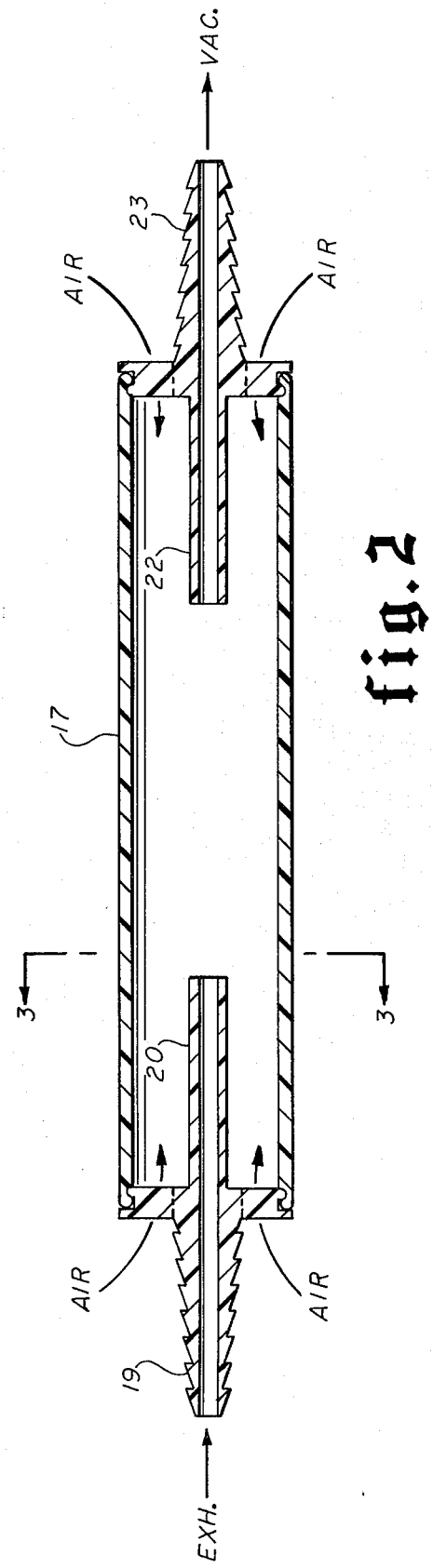
FIG. 2 is an enlarged side elevational view, in cross section, of the enlarged chamber.

In the drawings, the numeral 1 designates the male member of the control valve onto which the neck of the anesthesia breathing bag 2 is attached. An annular enlarged portion 3 of the male member is provided with raised markers 4, 4 to provide tactile indicia for the anesthetist. The female component 5, into which the male component 1 extends, also bears the raised markers 6. An annular ring 7 is formed on the outside surface of the member 1 and fits in the groove 8 in the inside wall of the female component 5, and a cutaway portion 8 of the male component provides an adjustable opening to the parabolic passageway 9 and tubular stem 10. An annular seal 11 is formed in the stem 10 consisting of a groove in which the annular projection 13 in the connecting member 14 is formed. The extended end of the connecting member 14 is annularly reduced and notched, as at 17', to receive the flexible hose 16 leading into the enlarged vacuum chamber 17. An annular groove 18 in the female component, in axial alignment with the parabolic passageway 9, permits a constant exhaust passageway through the valve.

The vacuum chamber 17 has the extended tapered hose receiving member 19, notched to anchor said hose 16 thereon, at a remote location from the bag 2, and is axially connected to the inwardly extended tube 20, which extends into the chamber 17. The end members of the chamber 17 are provided with air openings 21, 21 and at the discharge end of the chamber 17 another inwardly extending tubular member 22, is mounted, and an outwardly extended tapered, notched hose connection 23 extends from the said end of said chamber 17. A flexible hose 24 is connected to said last mentioned connection 23, and a vacuum pump (not shown) is remotely located from the said chamber 17 and maintains a vacuum on the chamber 17 and discharges into the free atmosphere, preferably outside of the operating room. The discharge end of the chamber 17 is constructed in the same manner as the other end member, having air passageways therethrough.

In use, the anesthetist starts the gas circuit, and controls the exhaust gas by means of the rotation of the male component, the raised portion thereof having raised indicia 4 and corresponding raised indicia on the female member, the center markers on each being longer than the markers on each side of the center marker, so that the anesthetist can feel the position of the markers and thus determine the position of the cutaway portion of the male member and consequently the degree of opening of the valve. Grip pads as 24 on the female component, and the area between the markers on the male member being knurled, assist in the careful and exact control of the valve. The parabolic tubular member provides a free passage of gas from the valve and the groove 18 permits constant exhaust into the parabolic member. The vacuum on the chamber 17 will constantly move the gas through the discharge hose, the air openings at each end of the chamber 17 permitting ample gas to satisfy the pull of the vacuum pump without exerting negative pressure on the hose 16, so that the flow from the valve will be controlled by the opening therein, and the pressure applied to the bag 2 during normal use. All of the exhaust gas will be thus captured by the chamber 17 and will be discharged where desired, remotely from the operating area.

What we claim is:

1. In a scavenger for an anesthesia circuit, a breathing bag equipped with a narrow neck, and a passageway therethrough, a valve mounted in the said neck of said bag, said valve having a tubular male member and a tubular female member in rotating telescoping relation, annular raised portions on said male member and female member for tactile reference to the position of the members relative to each other, a cutaway portion in a sidewall of said male member at the inserted end thereof, a parabolic passageway in a side wall of said female member adjacent said cutaway portion and which, by rotation of one of said members will be brought into and out of alignment with said cutaway portion of said male member, an enlarged chamber in flow alignment with said parabolic passageway, and a flexible hose leading from said parabolic passageway to said enlarged chamber, and means for maintaining a vacuum on said chamber.

2. The device defined in claim 1 wherein said female member has an annular groove formed therein, adjacent said parabolic passageway, to provide a constant exhaust passageway.

3. The device defined in claim 1 wherein a lateral tubular extension on said female member forms said parabolic passageway a hose connection mountable on said extension, a flexible hose mounted on said hose connection at one end, a vacuum chamber having hose connections at each end, the other end of said flexible hose being connected at one end of said chamber, and a tubular member mounted on one end of said chamber and extending inwardly therein, said tubular member being in axial alignment with said hose connection, and another flexible hose mounted on the other end of said chamber and extending to a remote discharge area, and means for maintaining a vacuum on said discharge end of said chamber.

4. The device defined in claim 3 wherein air inlets are provided in each end of said chamber.

5. The device defined in claim 3 wherein air inlets are formed in each end of said chamber, and an inwardly extending tubular member is mounted on the discharge end of said chamber, in axial alignment with said hose connection.

* * * * *

UNITED STATES PATENT AND TRADEMARK OFFICE
CERTIFICATE OF CORRECTION

PATENT NO. : 4,248,219                                    Page 1 of 2

DATED : February 3, 1981

INVENTOR(S) : Robert W. Moore, Jr. et al.

Figure 4:
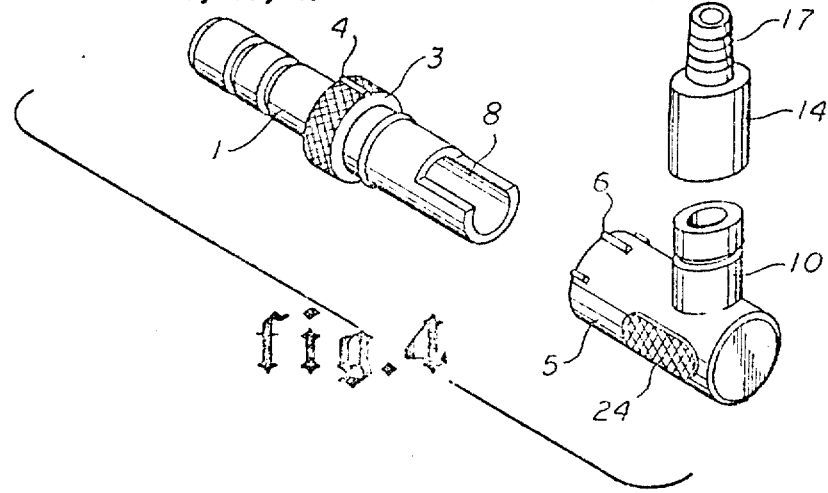
FIG. 4 is an extended side elevational view of the valve, illustrating the component parts thereof.
Figure 6:
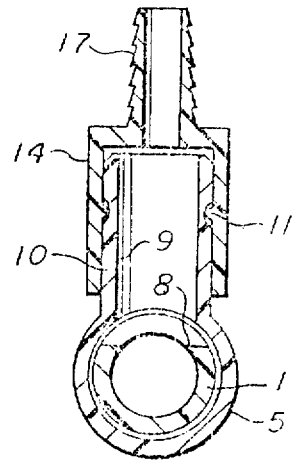
FIG. 6 is a cross sectional end view of the valve assembly taken on the line 6—6 of FIG. 5.
Figure 7:
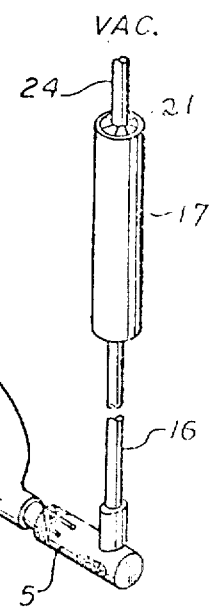
FIG. 7 is a fragmentary view of the completed scavenger assembly.
Figure 5:
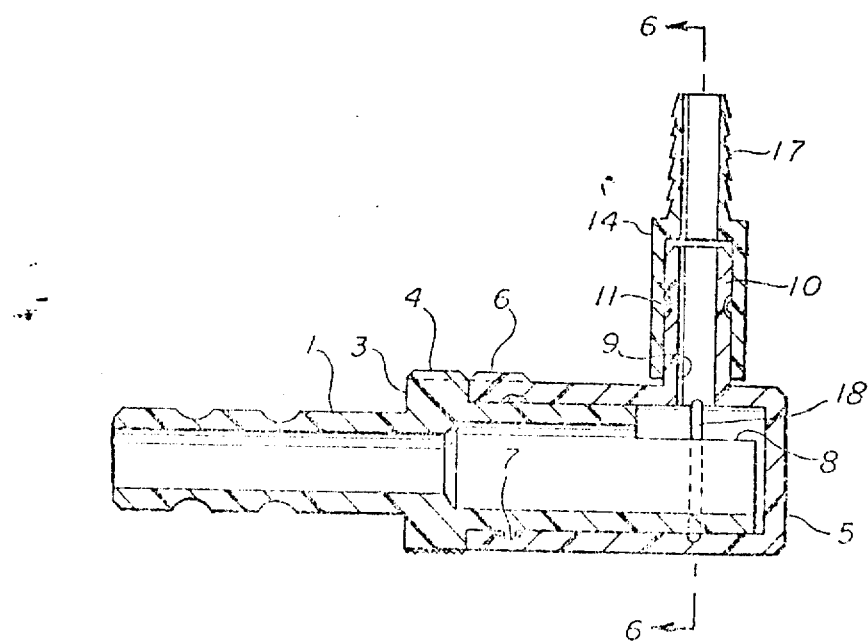
FIG. 5 is a cross sectional side view of the valve assembly.

It is certified that error appears in the above—identified patent and that said Letters Patent is hereby corrected as shown below:

Figures 4-7 should be added as shown on the attached sheet.

Signed and Sealed this

Nineteenth Day of May 1981

[SEAL]

Attest:

RENE D. TEGTMEYER

Attesting Officer     Acting Commissioner of Patents and Trademarks

Patent No. 4,248,219